United States Patent [19]

Saito

[11] Patent Number: 4,606,062
[45] Date of Patent: Aug. 12, 1986

[54] X-RAY COMPUTED TOMOGRAPHIC APPARATUS

[75] Inventor: Yasuo Saito, Ootawara, Japan
[73] Assignee: Kabushiki Kaishi Toshiba, Japan
[21] Appl. No.: 672,198
[22] Filed: Nov. 16, 1984
[30] Foreign Application Priority Data Nov. 18, 1983 [JP] Japan ................. 58-216006

[51] Int. Cl.[4] .................. A61B 6/00; G03B 41/16; H05G 1/60
[52] U.S. Cl. ..................... 378/13; 378/110; 378/112; 378/113
[58] Field of Search .............. 378/13, 19, 20, 110, 378/112, 113

[56] References Cited

U.S. PATENT DOCUMENTS 4,115,696 9/1978 Truscott ..................... 250/445
4,134,020 1/1979 Zonneveld .................. 250/445
4,200,799 4/1980 Saito ........................... 250/445
4,464,777 8/1984 Machida ..................... 378/13

Primary Examiner—Craig E. Church
Assistant Examiner—T. N. Grigsby
Attorney, Agent, or Firm—Finnegan, Henderson, Farabow, Garrett & Dunner

[57] ABSTRACT

An X-ray control device is held in a constant position relative to an X-ray tube and an X-ray detector, while the X-ray tube is moved toward or away from the rotational scanning axis at which an object to be examined is located. The X-ray control device allows selection of a spot size and a tube voltage of the X-ray tube. The X-ray control device is controlled in synchronism with a shift mechanism. When the X-ray tube is close to the object, a smaller spot and a higher tube voltage than those when the X-ray tube is separated from the object are selected.

6 Claims, 1 Drawing Figure

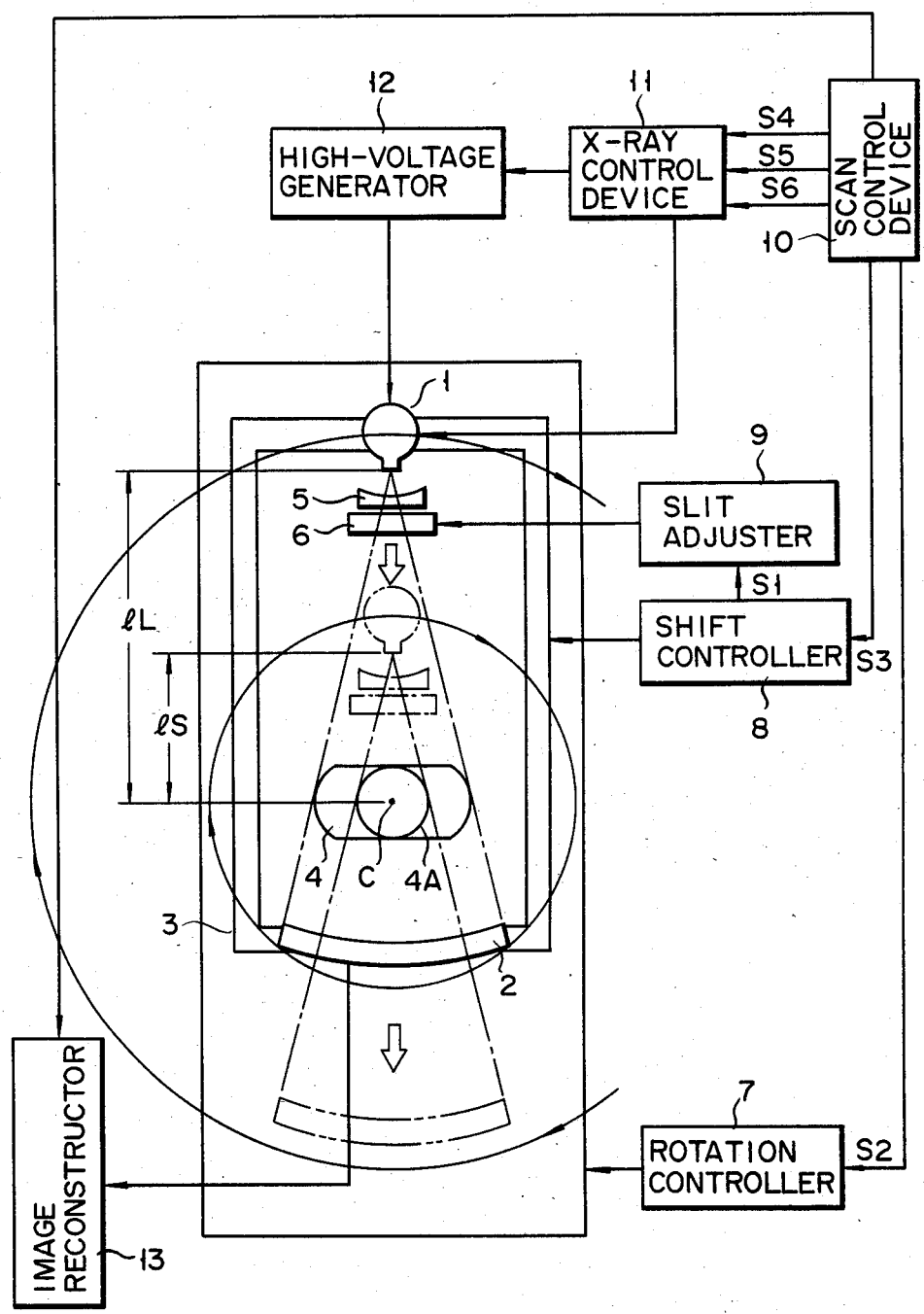

X-RAY COMPUTED TOMOGRAPHIC APPARATUS

BACKGROUND OF THE INVENTION

The present invention relates to an X-ray CT apparatus (X-ray computed tomographic apparatus) using a fan-shaped X-ray beam and, more particularly, to an X-ray CT apparatus which can produce X-rays of an optimal dose in accordance with a change in magnification corresponding to a change in the relative positional relationship between an X-ray tube and an object under examination.

In an X-ray CT apparatus using fan-shaped X-rays, a fan-shaped X-ray projection system consisting of an X-ray tube and an X-ray detector is rotated with respect to an object under examination. Projection data obtained from various angles within a predetermined slice of the object is acquired, and the obtained projection data is used for image reconstruction to obtain a slice image or a CT image. In some systems, when an object is imaged to obtain a CT image, the magnification of an image is changed by shifting the relative positional relationship between a fan-shaped beam X-ray projection system, consisting of an X-ray tube and an X-ray detector, and an imaging or scan field (the object is placed in this imaging field), formed near the center of rotation of the X-ray projection system along the radial direction of rotation of the system. The X-ray CT apparatus of this type is described in detail in U.S. Pat. No. 4,200,799.

When a CT image of an object having a small cross-section, e.g., the human head, is to be obtained with an X-ray CT apparatus as described in the above-mentioned patent, the X-ray projection system consisting of the X-ray tube and the X-ray detector is shifted with respect to its center of rotation to bring the tube and detector close together. X-rays are irradiated onto the object from the X-ray tube, the X-rays transmitted through the object are detected by the X-ray detector, and projection data is obtained in accordance with the detected result. In this case, since the occupying ratio of the object in the convergence angle of the fan-shaped beam is high, the X-ray detector can be utilized with high efficiency, and the magnification of the obtained CT image can also be high. However, in this case, the distance between the object and the X-ray detector is increased by a distance corresponding to a decrease in the distance between the X-ray tube and the object. Then, the half shade of the object on the detector is increased, and the obtained CT image is blurred.

In order to prevent such blurring of the CT image, the spot size of the X-ray tube can be decreased to a small spot size so as to reduce the half shade and to prevent blurring. However, in this case, if a small spot is simply used, the output of X-rays is decreased. Even if an attempt is made to compensate for such a decrease in the output of X-rays generated upon selection of a small spot, the degree of compensation is limited by the heat unit of an X-ray source. Thus, the X-ray dose cannot be increased to an acceptable value. When the output of X-rays decreases due to a small spot size, the dynamic range of X-ray projection data is lowered, the S/N ratio is degraded, and the image quality of the obtained CT image is degraded.

SUMMARY OF THE INVENTION

It is an object of the present invention to provide an X-ray CT apparatus which can produce a CT image of high quality even if the relative positional relationship between an imaging field and an X-ray projection system consisting of an X-ray tube and an X-ray detector is modified and the image magnification is changed in accordance with a change in a cross-section of an object under examination.

According to the present invention, in an X-ray CT apparatus wherein the relative positional relationship between an X-ray tube and an X-ray detector is maintained while a shift mechanism moves the X-ray tube toward and away from a rotational (scanning) axis at which the object is arranged, there is provided an X-ray CT apparatus wherein an X-ray control device which allows the selection of a spot size of the X-ray tube and a tube voltage of the X-ray tube is controlled in synchronism with the operation of the shift mechanism. When the X-ray tube is moved toward the object, a smaller spot size and a higher tube voltage are selected than those in the case wherein the X-ray tube is moved away from the object.

According to the present invention, the spot size of the X-ray tube is switched in accordance with the shift adjustment positions of the X-ray tube and the X-ray detector. When the small spot size is selected, a voltage applied to the X-ray tube is high. When the large spot size is selected, a voltage applied to the X-ray tube is low. Since the X-ray CT apparatus is controlled in this manner, the output of X-rays is kept substantially constant. An excellent S/N ratio can be obtained, and a CT image of high quality can be obtained.

BRIEF DESCRIPTION OF THE DRAWING

The single drawing is a block diagram of the X-ray CT apparatus according to an embodiment of the present invention.

DETAILED DESCRIPTION OF THE PREFERRED EMBODIMENT

In the X-ray CT apparatus according to an embodiment of the present invention, a function particular to the present invention is added to the apparatus disclosed in U.S. Pat. No. 4,200,799. The particular function described above includes a function whereby, while the relative positional relationship between an X-ray tube and an X-ray detector is kept unchanged, the X-ray tube is moved by a shift mechanism toward or away from a rotating scanning axis at which an object is arranged, thereby changing the spot size of the X-ray tube, and a function whereby the tube voltage of the X-ray tube is changed in synchronism with the operation of the shift mechanism.

As shown in the drawing, an X-ray tube 1 and an X-ray detector 2 are opposed to each other with a predetermined distance therebetween and are fixed on a common frame 3.

The X-ray tube 1 allows selection from a plurality of different spot sizes and generates a fan-shaped X-ray beam. The X-ray tube 1 can form spots of a plurality of different sizes and one desired size is selected. The X-ray tube 1 is constructed such that the spot position is substantially the same irrespective of which spot size is selected. In this embodiment, for the sake of descriptive convenience, the X-ray tube 1 is assumed to allow selection of one spot size from three spot sizes of large, intermediate and small corresponding to three imaging sizes or scanning sizes of large, intermediate and small.

The X-ray detector 2 generally comprises a number of detecting elements arranged in the form of an arc having the focal point of the X-ray tube 1 as the center and has a position detection sensitivity along the arc. Thus, the X-ray detector 2 can detect an X-ray intensity distribution along the arc.

An object such as a human body 4 is interposed between the X-ray tube 1 and the X-ray detector 2.

The frame 3 is supported on a rotary support (not shown). The rotary support is rotated by a rotary drive portion (not shown) about the position of the body 4. As the rotary support is rotated, the frame 3 is rotated. The frame 3 can be moved on the rotary support by a shift drive portion (not shown) so as to move the X-ray tube 1 toward or away from a center of rotation C at which the human body 4 is located. In this embodiment, the frame 3 can be set at three positions respectively corresponding to three different distances of long, intermediate and short (respectively corresponding to three scan sizes of large, intermediate and small) between the X-ray tube and the center of rotation.

A dose compensation filter 5 and a fan-beam-thickness-adjusting-variable slit 6 are arranged at the incident port of the X-ray tube 1.

The filter 5 is arranged to compensate for the influence of the distribution of the X-ray path in the human body 4. The filter 5 comprises a wedged filter which consists of a substance having a relatively low X-ray absorption coefficient, has a wedge shape which is thin at the center along the widthwise direction of the fan-shaped X-ray beam transmitted through the filter 5, and is thick at the sides. A slice of the human body 4 has a substantially elliptical shape which is thick at the center and which is thin at the sides. Therefore, the X-ray path in the human body 4 due to projection of such a fan-shaped X-ray is long at the center and short at the sides. The wedged filter 5 imparts an X-ray path distribution which is substantially inverse to that in the human body 4 so as to compensate for the X-ray dose on the X-ray detector 2 and to reduce differences in the X-ray dose at various positions of the X-ray detector 2. Such compensation is performed so as to reduce the dynamic range of the detected value of the X-ray detector 2 and to allow easy and highly reliable processing of projection data.

The slit 6 determines the thickness of the fan-shaped X-rays. The X-rays emitted from the X-ray tube 1 are passed through the slit 6 and shaped into a flat sector shape and are thereby converted into a fan-shaped X-ray beam. The slit 6 has a variable opening width. When the opening width of the slit 6 is changed, the thickness of the fan-shaped X-ray beam is adjusted. In this embodiment, it is assumed that the opening width of the slit 6 can be changed among the three different sizes of wide, intermediate and narrow (corresponding to the large, intermediate and small scan sizes).

The filter 5 and the slit 6 are supported on the X-ray tube 1 directly or indirectly and are moved together upon the rotational movement of the frame 3.

A rotation controller 7 is coupled to the rotary drive portion described above. The rotation controller 7 directly controls the rotary drive portion and indirectly controls the frame rotation. A shift controller 8 is coupled to the shift drive portion described above. The shift controller 8 directly controls the shift drive portion and indirectly moves the frame 3 such that the X-ray tube 1 is moved toward or away from the center of rotation C at which the human body 4 is located. A slit adjuster 9 is connected to the shift controller 8 to receive a control signal S1 therefrom. The slit adjuster 9 controls the slit 6 to ajust the slit width.

A scan control device 10 controls X-ray projection scanning and generally comprises a computer incorporated within a console. The rotation controller 7, the shift controller 8 and an X-ray control device 11 are connected to the scan control device 10. A rotation control signal S2 for projection scanning of the fan-shaped X-ray beam is supplied from the scan control device 10 to the rotation controller 7. In response to the signal S2, the rotation controller 7 rotates the frame 3. A size signal S3 indicating a scan size selected in accordance with the size of the human body 4 (strictly speaking, the cross-sectional area) is supplied from the scan control device 10 to the shift controller 8. In response to the signal S3, the shift controller 8 moves the frame 3 in the manner described above. The control signal S1 supplied from the shift controller 8 to the slit adjuster 9 corresponds to this size signal S3. The scan control device 10 supplies to the X-ray control device 11 an irradiation command signal S4, a tube voltage selection signal S5 and a spot selection signal S6 for the X-ray tube 1. The signal S4 instructs a start and end of X-ray irradiation. The signal S5 is for selecting the tube voltage, and the signal S6 is for setting the spot size of the X-ray tube 1.

The X-ray tube 1 and a high voltage generator 12 are connected to the X-ray control device 11, and the X-ray tube 1 is connected to the high voltage generator 12. The X-ray control device 11 controls the high voltage generator 12 in response to the signals S4 and S5 and controls the X-ray tube 1 in response to the signal S6. The spot of the size of the X-ray tube 1 is selected by the X-ray control device 11 in accordance with the signal S6. The X-ray tube 1 receives a tube current predetermined by the high voltage generator 12 and a tube voltage corresponding to the signal S5 to generate X-rays. The beginning and end of X-ray irradiation is controlled by the X-ray controller 11 through the high voltage generator 12 in response to the signal S4.

Projection data detected by the X-ray detector 2 is acquired in an image reconstructor 13 which is associated with the rotation scan of the scan control device 10. Image reconstruction is thus performed, and a reconstructed image or a CT image is thus obtained. The CT image obtained by the image reconstructor 13 is displayed by an image display means (not shown) and/or stored in a memory (not shown). The image reconstructor 13 generally comprises a computer, and in many cases, at least the CPU (central processing unit) of the computer is commonly used as a CPU for the scan control device 10.

As illustrated in the drawing, when the distance between the X-ray tube 1 and the center of rotation C as the center of an imaging field is lL, the imaging field is large (L size). When this distance is lS, the imaging field is small (S size). Although not shown in the drawing, when this distance is intermediate between lL and lS, the imaging field size is intermediate (M size). Note that lL>lM>lS. These scan sizes are selectively used. For example, the L size is for the abdomen or thorax of an obese person, the M size is for the abdomen or thorax of a thin person, and the S size is for a head of a person.

The mode of operation of the X-ray CT apparatus having the construction as described above will be described below.

Before the description, the following assumptions are made: the M size is selected as the scan size, the X-ray tube 1 and the X-ray detector 2 are located to obtain the scan size of M size (the distance lM between the X-ray tube 1 and the center of rotation C), the X-ray tube 1 is set to have the intermediate spot size, the tube voltage VM is selected, and the intermediate opening width of the slit 6 is selected.

In order to obtain a CT image of a human head 4A, the S size is selected.

When the S size is selected by the scan control device 10, the size signal S3 corresponding to the S size is supplied to the shift controller 8. The shift controller 8 then drives the shift drive portion, and the frame 3 is moved with respect to the center of rotation C. Thus, the X-ray tube 1 and the X-ray detector 2 are moved to the positions corresponding to the S size (the distance lS between the X-ray tube 1 and the X-ray detector 2). Then, the shift controller 8 starts the shifting operation and supplies a control signal S1 to the slit adjuster 9 so as to change the opening width of the slit 6 from wide to narrow.

At the same time, the tube voltage selection signal S5 and the spot selection signal S6 are supplied from the scan control device 10 to the X-ray control device 11. The X-ray control device 11 controls the X-ray tube 1 to change the spot to the small spot size. The X-ray control device 11 controls the high voltage generator 4 to select a tube voltage corresponding to the tube voltage selection signal S5. Then, a tube voltage VS corresponding to the S size and higher than the tube voltage VM corresponding to the M size is applied to the X-ray tube 1.

In this manner, when the S size is selected, the small spot size is selected for the spot of the X-ray tube 1, and the tube voltage VS is selected as a tube voltage of the X-ray tube 1.

In this state, a rotation control signal S2 is supplied from the scan control device 10 to the rotation controller 7, and the frame 3 is driven at predetermined angular intervals in a stepwise manner. In synchronism with this rotation, an irradiation command signal S4 is supplied from the scan controller 10 to the X-ray control device 11. The fan-shaped X-ray is intermittently irradiated onto the head 4A of the human body 4 at each angular step, and X-ray transmission data is detected by the X-ray detector 2.

The X-ray transmission data detected by the X-ray detector 2 is acquired at the image reconstructor 13 to be subjected to image reconstruction. A CT image obtained at the image reconstructor 13 is supplied to an image display portion (not shown) and is displayed on a display screen of the image display.

The relationships between the voltage and the X-ray dose of the X-ray tube 1 and that between the tube voltage and the spot temperature are: the X-ray dose is the third power of the tube voltage and the spot temperature is the second power of the tube voltage.

Thus, as described above, when the voltage VS applied to the X-ray tube 1 when the S size is selected is larger than the voltage VM, a decrease in the X-ray dose as compared to the case wherein the M size is selected is prevented. Furthermore, an increase in the spot temperature of the X-ray tube 1 accompanying such a decrease in the X-ray dose is reduced to a minimum. Therefore, even when compensation for a decrease in the X-ray dose is performed when the small spot is selected, the spot temperature will not exceed a predetermined heat unit.

When the L or M size is selected as the scan size, the distance between the X-ray tube 1 and the center of rotation C is selected to be lL and lM. The opening width of the slit 6 is selected to be wide and intermediate. The spot size of the X-ray tube 1 is selected to be large or intermediate. The tube voltage applied to the X-ray tube 1 is selected to be VL or VM (where $VL < VM < VS$).

In this manner, since the X-ray dose from the X-ray tube 1 is kept substantially constant irrespective of the L, M or S size, the X-ray transmission data detected by the X-ray detector 2 will not change greatly for each size. Therefore, a difference in the image quality on the display screen due to a change in the scan size will be reduced to a minimum.

In the above description, the signals S3 and the signals S5 and S6 are simultaneously supplied from the scan control device 10 to the shift controller 8 and the X-ray controller 11 so as to select the spot size and the tube voltage in synchronism with the shift operation. However, a similar effect can be obtained if a means is provided to supply the tube voltage selection signal S5 and the spot selection signal S6 directly to the X-ray controller 11 in response to the shift controller 8 while the shift signal S3 is supplied from the scan control device 10 to the shift controller 8 to perform a shift operation.

As factors in compensating for the irradiation X-ray dose with a change in the spot size synchronous with the shift operation, not only the tube voltage but also the tube current may be changed.

What is claimed is:

1. An X-ray computed tomographic apparatus comprising:

X-ray generating means, having an X-ray tube and a plurality of X-ray spot sizes to be selected, for generating a fan-shaped X-ray beam onto an object to be examined;

setting means having at least means for setting an X-ray tube voltage of said X-ray generating means, means for setting a start/stop of X-ray irradiation by said X-ray generating means, and means for setting an X-ray spot size of said X-ray generating means;

an X-ray detector having a position sensitivity in at least one direction;

rotating means for supporting said X-ray generating means and said X-ray detector to oppose each other and for rotating said X-ray generating means and said X-ray detector about an axis therebetween at which the object is arranged;

shift adjusting means for integrally shifting said X-ray generating means and said X-ray detector with respect to the axis which is a center of rotation of a rotational movement provided by said rotating means, and for adjusting a distance between said X-ray generating means and said X-ray detector so as to match a width of the fan-shaped X-ray beam with a range of the object;

scan control means for controlling said rotating means and said setting means so as to rotate said X-ray generating means and said X-ray detector around the object and for irradiating the object with the fan-shaped X-ray beam for each predetermined projection angle; and image reconstructing means for acquiring projection data obtained from said X-ray detector upon irradiation of the fan-shaped X-ray beam at various angles, said means for setting the X-ray spot size being interlocked with said shift adjusting means so as to select, when said X-ray generating means and the object are close to each other, a spot size smaller than that in the case wherein said X-ray generating means and the object are separated from each other, and said means for setting the tube voltage being interlocked with said shift adjusting means so as to select, when said X-ray generating means and the object are close to each other, a tube voltage higher than that in the case wherein said X-ray generating means and the object are separated from each other.

2. An apparatus according to claim 1, wherein said setting means includes means for selecting a tube current in synchronism with a selection of the tube voltage.

3. An apparatus according to claim 1, wherein said scan control means controls X-ray control means so as to allow said X-ray generating means to intermittently generate the X-ray beam at each projection angle.

4. An apparatus according to claim 1, further comprising an X-ray beam thickness control slit which is interposed between said X-ray generating means and the object and has an opening variable in a direction of thickness of the X-ray beam generated by said X-ray generating means, and slit control means for controlling said slit so as to select, when said X-ray generating means and the object are close to each other, an opening wider than that in the case wherein said X-ray generating means and the object are separated from each other.

5. An apparatus according to claim 1, further comprising a wedged filter which is interposed between said X-ray generating means and the object and which reduces an influence of a difference in a thickness of the object according to a position of the X-ray beam generated by said X-ray generating means.

6. An apparatus according to claim 1, wherein said scan control means simultaneously generates a setting signal to at least one of said means for setting the tube voltage and said means for setting the spot size, and a shift command signal to said shift adjusting means.

* * * * *

UNITED STATES PATENT AND TRADEMARK OFFICE
CERTIFICATE OF CORRECTION

PATENT NO. : 4,606,062
DATED : August 12, 1986
INVENTOR(S) : YASUO SAITO

It is certified that error appears in the above-identified patent and that said Letters Patent is hereby corrected as shown below:

Claim 1, line 40, change "separated" to -- far --; and line 45, change "separated" to -- far --.

Signed and Sealed this

Twenty-fifth Day of November, 1986

Attest:

DONALD J. QUIGG

Attesting Officer      Commissioner of Patents and Trademarks